United States Patent
Ford et al.

(10) Patent No.: US 10,300,059 B2
(45) Date of Patent: *May 28, 2019

(54) PHARMACEUTICAL COMPOSITION AND THERAPEUTIC COMBINATION COMPRISING A CHOLESTERYL ESTER TRANSFER PROTEIN INHIBITOR AND HMG COA REDUCTASE INHIBITORS

(71) Applicant: DEZIMA PHARMA B.V., Thousand Oaks, CA (US)

(72) Inventors: John Ford, Cambridgeshire (GB); Patrick Round, Cambridgeshire (GB); John Kastelein, Suffolk (GB)

(73) Assignee: DEZIMA PHARMA B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/507,669

(22) PCT Filed: Aug. 3, 2015

(86) PCT No.: PCT/NL2015/050562
§ 371 (c)(1),
(2) Date: Feb. 28, 2017

(87) PCT Pub. No.: WO2016/032324
PCT Pub. Date: Mar. 3, 2016

(65) Prior Publication Data
US 2018/0000818 A1    Jan. 4, 2018

(30) Foreign Application Priority Data
Aug. 28, 2014 (WO) ............... PCT/NL2014/050584

(51) Int. Cl.
*A61K 31/506* (2006.01)
*A61K 31/513* (2006.01)
*A61K 31/202* (2006.01)
*A61K 31/40* (2006.01)
*A61K 31/505* (2006.01)
*A61K 45/06* (2006.01)

(52) U.S. Cl.
CPC .......... *A61K 31/506* (2013.01); *A61K 31/202* (2013.01); *A61K 31/40* (2013.01); *A61K 31/505* (2013.01); *A61K 31/513* (2013.01); *A61K 45/06* (2013.01)

(58) Field of Classification Search
CPC .... A61K 31/506; A61K 31/202; A61K 31/40; A61K 31/505; A61K 31/513; A61K 45/06
USPC ......................................................... 514/275
See application file for complete search history.

(56) References Cited

U.S. PATENT DOCUMENTS

| | | | | |
|---|---|---|---|---|
| 6,489,478 B1* | 12/2002 | DeNinno | ............ | C07D 215/42 546/159 |
| 7,872,126 B2* | 1/2011 | Kubota | ............... | C07D 215/42 544/298 |
| 2007/0269507 A1* | 11/2007 | Sachetto | ............. | A61K 9/4825 424/456 |
| 2017/0182048 A1* | 6/2017 | Ford | .................... | A61K 31/506 |

FOREIGN PATENT DOCUMENTS

| | | |
|---|---|---|
| JP | 2007/119450 A1 | 5/2007 |
| WO | 2000/17165 A1 | 3/2000 |
| WO | 2005/095409 A2 | 10/2005 |
| WO | 2013/169797 A1 | 11/2013 |

OTHER PUBLICATIONS

Niesor EJ et al., "Statin-Induced Decrease in ATP-Binding Cassette Transporter A1 Expression via microRNA33 Induction may Counteract Cholesterol Efflux to High-Density Lipoprotein," *Cardiovasc Drugs Ther*; 29: 7-14 (2015).

* cited by examiner

*Primary Examiner* — Yevgeny Valenrod
(74) *Attorney, Agent, or Firm* — Elsa Lemoine

(57) ABSTRACT

The present invention relates to a pharmaceutical composition and a therapeutic combination comprising a novel cholesteryl ester transfer protein (CETP) inhibitor and a HMG CoA Reductase inhibitor, which may be used in the treatment of subjects suffering from or having an increased risk for cardiovascular diseases, in particular hyperlipidemia or mixed dyslipidemia.

15 Claims, 1 Drawing Sheet

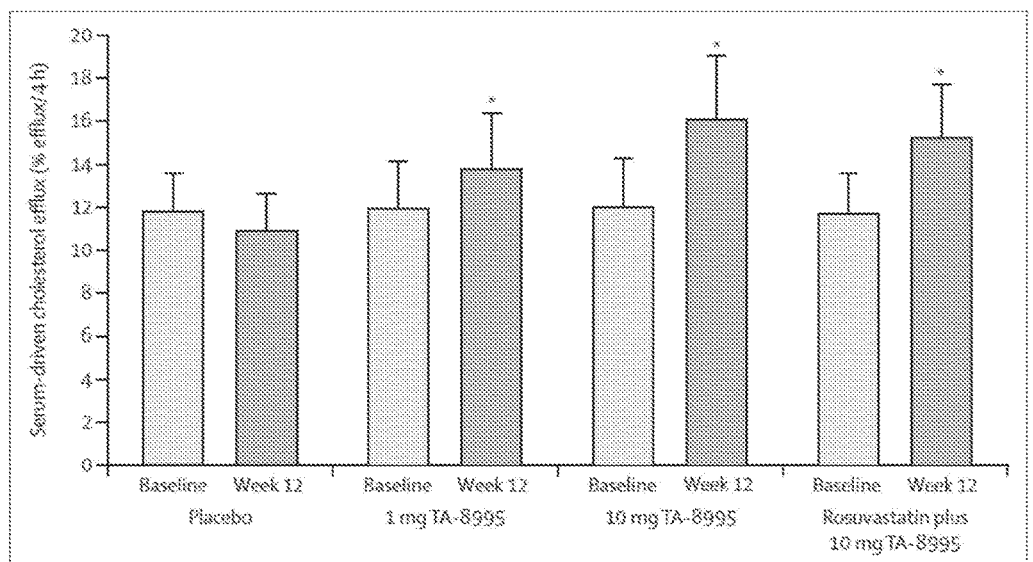

PHARMACEUTICAL COMPOSITION AND THERAPEUTIC COMBINATION COMPRISING A CHOLESTERYL ESTER TRANSFER PROTEIN INHIBITOR AND HMG COA REDUCTASE INHIBITORS

CROSS REFERENCES TO RELATED APPLICATIONS

This application is a National Stage Application under 35 U.S.C. § 371 of International Application No. PCT/NL2015/050562, having an international filing date of Aug. 3, 2015, which is claiming priority from an International Application No. PCT/NL2015/050584, having an international filing date of Aug. 28, 2014.

TECHNICAL FIELD OF THE INVENTION

The present invention relates to a pharmaceutical composition and a therapeutic combination comprising a novel cholesteryl ester transfer protein (CETP) inhibitor and a HMG CoA Reductase inhibitor, which may be used in the treatment of subjects suffering from or having an increased risk for cardiovascular diseases, in particular hyperlipidemia or mixed dyslipidemia.

BACKGROUND OF THE INVENTION

Prospective epidemiological studies have shown a strong association between low density lipoprotein-cholesterol (LDL-C) levels and cardiovascular disease (CVD) risk.

Hydroxy-methylglutaryl coenzyme A reductase (hereinafter: HMG CoA reductase) is an enzyme in the lever that functions in the production of cholesterol. Inhibition of HMG CoA reductase by HMG CoA reductase inhibitors, commonly referred to as "statins", has been shown to reduce the level of LDL-C in the blood by reducing the production and accelerating uptake of cholesterol. The application of such statin therapy to decrease these LDL-C levels in the blood have resulted in a marked reduction of CVD-related morbidity and mortality. However, there are safety issues associated with HMG CoA reductase inhibitors. Particularly at high doses, they may cause increases in liver enzymes and myopathy and occasionally rhabdomyolysis, which may lead to death from acute reneal failure.

Furthermore, several studies have shown that also a low plasma concentration of high-density lipoprotein (HDL-C) is a powerful risk factor for the development of cardiovascular diseases. One new approach which reduces LDL-C and elevates HDL-C levels is to inhibit the Cholesterol Ester Transfer Protein (CETP). CETP is a plasma protein secreted primarily by liver and adipose tissue. CETP mediates the transfer of cholesteryl esters from HDL to apolipoprotein B (A Apo B)-containing particles (mainly LDL and VLDL) in exchange for triglycerides, thereby decreasing the cholesterol content in HDL in favor of that in (V)LDL. Hence, CETP inhibition has been hypothesized to retain cholesteryl esters in HDL-C and decrease the cholesterol content of the atherogenic Apo B fraction.

Despite the evidence supporting the potential of CETP inhibition in reducing cardiovascular morbidity, clinical development of CETP inhibitors has not been straightforward. The first compound to progress to phase 3 clinical trials was torcetrapib which was dosed at 60 mg. Torcetrapib was shown to increase HDL-C by 72% and decrease LDL-C by 25%, but it was subsequently withdrawn from development owing to safety concerns including an unexpected increase in cardiovascular events and death when used in combination with the HMG CoA reductase inhibitor atorvastatin.

Although the mechanism of those events is not fully understood, there is increasing evidence that they might have been due to off-target effects of torcetrapib such as increased blood pressure, changes in electrolytes (increases in sodium and bicarbonate and decreases in potassium) and increases in aldosterone, consistent with mineralocorticoid activity. There is also some evidence from animal studies that torcetrapib increases expression of endothelin-1, which has been postulated to be have contributed to the apparent (non-significant) increase in cancer deaths in the ILLUMINATE trial. These observations could be related to the relatively high dose of torcetrapib needed.

Subsequently, another CETP inhibitor, dalcetrapib, entered clinical trials. Dalcetrapib was shown to be a weak inhibitor that increased HDL-C by 30-40% with minimal effects on LDL-C concentrations. Dalcetrapib development has also been terminated on the grounds of futility in a Phase 3 study where the drug was dosed at 600 mg. Lack of efficacy was probably related to modest CETP inhibition (18).

Two more CETP inhibitors, anacetrapib and evacetrapib, are currently in phase 3 clinical trials. Data from phase 2 studies suggest that both are CETP inhibitors without mineralocorticoid activity. Anacetrapib 200 mg once daily has been shown to increase HDL C by 97% and decrease LDL-C by 36% in fasted healthy subjects (21) and 150 mg once daily anacetrapib has been shown to increase HDL C by 139% and decrease LDL-C by 40% in patients (22). However, anacetrapib accumulates in fat tissue and as a consequence of this has a undesirable half life of 2-4 years in humans. Evacetrapib (500 mg once daily monotherapy in patients) has been shown to increase HDL-C by 129% and decrease LDL-C by 36% (23).

In the ongoing Phase 3 studies, a once daily dose of 100 mg anacetrapib is being clinically evaluated, whereas for evacetrapib a once daily dose of 130 mg is being evaluated. Such relatively high amounts of active ingredients may however lead to serious problems, and may present serious issues when formulating combination products thereof.

A disadvantage of the use of the known CETP-inhibitors is that due to the relatively high dosage which has to be used to obtain CETP-inhibition, more and stronger side effects may occur. This can have a negative influence on both the physical well-being of the patient as well as on patient compliance.

It has thus been difficult to use CETP-inhibitors in combination with other pharmaceutically active compounds. More particularly, in view of the existing side effects of HMG CoA reductase inhibitors and the relatively high dose of the known CETP-inhibitors, combining these inhibitors in a pharmaceutical combination has proven to be problematic, as has been observed when the combination of Torcetrapib and atorvastatin was clinically tested.

Hence, a continuing need remains to find convenient, safe and effective agents or combination of agents for use in the treatment of subjects suffering from or having an increased risk for cardiovascular diseases.

SUMMARY OF THE INVENTION

A first aspect of the present invention relates to a pharmaceutical composition comprising:
(a) a compound of the formula:

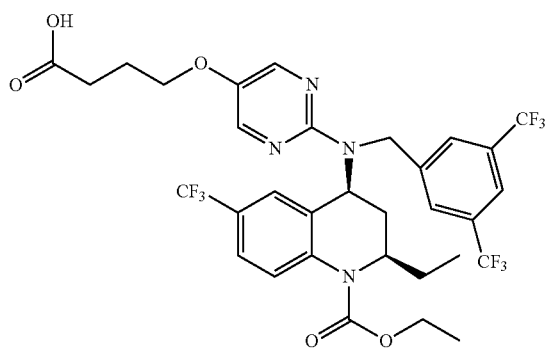 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

(hereinafter: Compound A) or a pharmaceutically acceptable salt thereof;
(b) at least one HMG CoA reductase inhibitor or a pharmaceutically acceptable salt thereof; and
(c) one or more pharmaceutically acceptable excipients.

A second aspect of the present invention relates to a therapeutic combination comprising said Compound A and at least one HMG CoA reductase inhibitor or a pharmaceutically acceptable salt thereof.

A third aspect of the present invention relates to the use of the pharmaceutical composition or the therapeutic combination in the treatment of subjects suffering from or having an increased risk for cardiovascular diseases.

Clinical studies have shown that compared to other known CETP-inhibitors only a relatively low dose of Compound A is needed to significantly increase the HDL-C concentration and significantly lower the LDL-C concentration. This makes Compound A particularly suitable to be used in combination with other pharmaceutically active compounds. It has further been shown in clinical studies that combining Compound A with HMG CoA reductase inhibitors gives a synergistic effect with respect to the lowering of the LDL-C concentration in blood and that it does not lead to serious side effects. In other words, when Compound A is used in combination with a HMG CoA reductase inhibitor, such as atorvastatin or rosuvastatin, the LDL-C concentration decreases more than when these compounds are used separately. Furthermore, with the present invention it is possible to use a lower dose of HMG CoA reductase inhibitor than conventionally used, thereby overcoming possible intolerance to these types of inhibitors. In addition, it has also been found that Compound A alone and in combination with statins enhanced the ability of serum to promote cholesterol efflux.

Definitions

The term 'pharmaceutical composition' as used herein has its conventional meaning and refers to a composition which is pharmaceutically acceptable.

The term 'pharmaceutically acceptable' as used herein has its conventional meaning and refers to compounds, material, compositions and/or dosage forms, which are, within the scope of sound medical judgment suitable for contact with the tissues of mammals, especially humans, without excessive toxicity, irritation, allergic response and other problem complications commensurate with a reasonable benefit/risk ratio.

The term 'excipient' as used herein has its conventional meaning and refers to a pharmaceutically acceptable ingredient, which is commonly used in the pharmaceutical technology for preparing a granulate, solid or liquid oral dosage formulation.

The term 'salt' as used herein has its conventional meaning and includes the acid addition and base salts of Compound A.

The term 'increased risk' has its conventional meaning and refers to a situation in a subject, preferably human, where in individuals, either male or female, have an LDL-cholesterol level above 2.6 mmol/l, such that they are exposed at an increased risk of a cardiovascular event, compared to those with lower levels.

The term 'treatment' as used herein has its conventional meaning and refers to curative, palliative and prophylactic treatment.

The term 'cardiovascular disease' as used herein has its conventional meaning and includes arteriosclerosis, peripheral vascular disease, hyperlipidemia, mixed dyslipidemia betalipoproteinemia, hypoalphalipoproteinemia, hypercholesteremia, hypertriglyceridemia, familial-hypercholesteremia, angina, ischemia, cardiac ischemia, stroke, myocardial infarction, reperfusion injury, restenosis after angioplasty, hypertension, cerebral infarction and cerebral stroke.

The term 'HMG-CoA reductase inhibitor' as used herein has its conventional meaning and is used interchangeably with the term 'statins' and refers to compounds which are used to lower LDL-C by inhibiting the enzyme HMG-CoA reductase. Well known HMG-CoA reductase inhibitors are atorvastatin, pravastatin, fluvastatin, simvastatin, lovastatin, rosuvastatin and pitavastatin.

The term 'unit dosage form' has its conventional meaning and refers to a dosage form which has the capacity of being administered to a subject, preferably a human, to be effective, and which can be readily handled and packaged, remaining as a physically and chemically stable unit dose comprising the therapeutic agent, i.e. Compound A or combination of therapeutic agents, such as Compound A and a HMG CoA reductase inhibitor.

The term 'fixed dose combination' as used herein has its conventional meaning and refers to a combination of defined doses of two or more drugs or active ingredients presented in a single dosage unit (e.g. a tablet or a capsule) and administered as such.

The term 'free dose combination' as used herein has its conventional meaning and refers to a combination of two drugs or active ingredients administered simultaneously but as two distinct dosage units.

BRIEF DESCRIPTION OF THE DRAWINGS

FIG. 1 shows baseline and week 12 data for serum-driven cholesterol efflux. Bars are means and error bars are standard deviations. The baseline data only includes patients who had both baseline and week 12 data. The changes from baseline for all active treatments showed significant differences from placebo at week 12.

DETAILED DESCRIPTION OF THE INVENTION

A first aspect of the present invention relates to a pharmaceutical composition comprising:
(a) a compound of the formula:

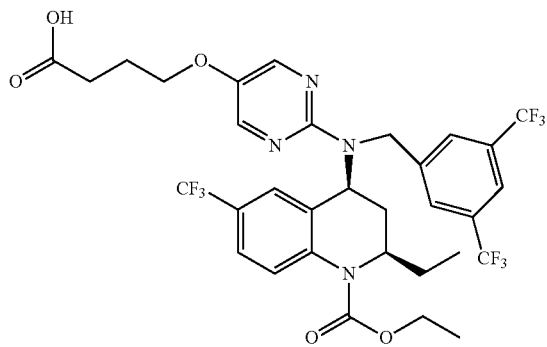 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

(hereinafter: Compound A) or a pharmaceutically acceptable salt thereof;
(b) at least one HMG CoA reductase inhibitor or a pharmaceutically acceptable salt thereof; and
(c) one or more pharmaceutically acceptable excipients.

Compound A as such has already been described in the European patent application EP1730152, wherein it has been identified as a CETP-inhibitor among many other CETP-inhibitors. Surprisingly, clinical studies have now shown that compared to other known CETP-inhibitors only a relatively low dose of Compound A is needed to significantly increase the HDL-C concentration and significantly lower the LDL-C concentration. This makes Compound A particularly suitable to be used in combination with other pharmaceutically active compounds.

It has now surprisingly been shown in clinical studies that combining Compound A with HMG CoA reductase inhibitors gives a synergistic effect with respect to the lowering of the LDL-C concentration in blood. In other words, when Compound A is used in combination with a HMG CoA reductase inhibitor, such as atorvastatin or rosuvastatin, the LDL-C concentration decreases more than when these compounds are used separately. Moreover, no serious side effects have been observed by using a combination of these compounds.

The pharmaceutical composition according to the present invention is therefore preferably used in the treatment of subjects suffering from or having an increased risk for cardiovascular diseases. Said pharmaceutical composition is more preferably used in the treatment of subjects suffering from or having an increased risk for hyperlipidemia or mixed dyslipidemia.

Furthermore, with the present invention it is possible to use a lower dose of HMG CoA reductase inhibitor than conventionally used, thereby overcoming possible intolerance to these types of inhibitors. In addition, it has also been found that Compound A alone and in combination with statins enhanced the ability of serum to promote cholesterol efflux. As has been described in Niesor E J, et al., Cardiovasc Drugs Ther. 2015 February; 29(1):7-14, statins generally have a tendency to decrease cholesterol efflux. It has now remarkably been found that this can be avoided when said statins are used in combination with Compound A.

Compound A is preferably used together with a HMG CoA reductase inhibitor which is selected from the group consisting of atorvastatin, pravastatin, fluvastatin, simvastatin, lovastatin, rosuvastatin and pitavastatin.

More preferably, the HMG CoA reductase used is atorvastatin calcium, pravastatin sodium, fluvastatin sodium, simvastatin, lovastatin and rosuvastatin calcium. These inhibitors have been used in many patients for many years and have shown to be able to significantly reduce the LDL-C concentration in patients.

The pharmaceutical composition according to the present invention preferably comprises 1 to 25 mg of Compound A and 1 to 80 mg of the HMG CoA reductase inhibitor. Alternatively, the pharmaceutical composition according to the present invention comprises 1 to 25 mg of Compound A and 1 to 50 mg, optionally 1 to 30 mg or 1 to 20 mg of the HMG CoA reductase inhibitor In a further embodiment of the pharmaceutical composition according to the present invention the composition comprises 5 to 10 mg of Compound A and 1 to 20 mg of HMG CoA reductase inhibitor.

Due to the synergistic effect between Compound A and HMG CoA reductase inhibitors it is now surprisingly also possible to lower the amount of HMG CoA reductase inhibitors used, thereby avoiding side effects commonly observed in these kinds of pharmaceutical compounds. In this regard it is also noted that such lower doses could also overcome intolerance to HMG CoA reductase inhibitors, which is also referred to as statin intolerance.

The pharmaceutical composition according to the present invention is preferably administered orally to subjects in need thereof. Oral administration may involve swallowing, so that the pharmaceutically active compounds enter the gastrointestinal tract. Specific pharmaceutical preparations, as described below, may be developed which facilitate the oral administration.

The pharmaceutical composition according to the present invention is preferably formulated as an oral free dose combination or as an oral fixed dose combination. The different pharmaceutically active ingredients may be present in said combinations as granulates. Preferably, the pharmaceutical composition is an oral fixed dose combination, such a combination is very convenient for patients and avoids problems with administering the correct amounts of these compounds.

Solid oral dosage forms which may be used within the context of the present invention include besides tablets and capsules amongst others caplets, lozenges, pills, mini-tablets, pellets, beads and granules. Liquid oral dosage forms which may be used for the pharmaceutical preparation of the present invention include, but are not limited to drinks, solutions, suspensions, syrups, beverages and emulsions.

The oral fixed dose combination or oral free dose combination is preferably formulated as a solid dosage form, such as a tablet or capsule. Generally, the administration of these kinds of formulations is considered to be the most convenient for patients.

In a particularly preferred embodiment the pharmaceutical composition according to the present invention is an oral fixed dose combination comprising 1 to 25 mg of Compound A and 1 to 80 mg of atorvastatin, pravastatin, fluvastatin, simvastatin, lovastatin, rosuvastatin or pitavastatin, preferably atorvastatin or rosuvastatin. In an even further embodiment thereof, said pharmaceutical composition comprises 1 to 25 mg of Compound A and 1 to 20 mg of said HMG CoA reductase inhibitors.

Besides Compound A and the HMG CoA reductase inhibitors as such, pharmaceutically acceptable salts thereof may also be used in the pharmaceutical composition according to the present invention. Pharmaceutically acceptable salts of Compound A and the HMG CoA reductase inhibitors include the acid addition and base salts thereof, such as preferably the calcium, potassium or sodium salts. For a review on suitable salts, reference is made "Handbook of Pharmaceutical Salts: Properties, Selection, and Use" by Stahl and Wermuth (Wiley-VCH, Weinheim, Germany, 2002).

A pharmaceutically acceptable salt of Compound A or of HMG CoA reductase inhibitors may be readily prepared by mixing together solutions of such compounds and the desired acid or base, as appropriate. The salt may precipitate from solution and be collected by filtration or may be recovered by evaporation of the solvent.

The present invention also relates to the use of pharmaceutically acceptable solvates or pro-drugs of Compound A and/or pharmaceutically acceptable solvates or pro-drugs of the HMG CoA reductase inhibitors in the pharmaceutical composition of the present invention.

In a further embodiment of the present invention, the composition according the present invention comprises polyunsaturated fatty acids (PUFAs), preferably omega-3 polyunsaturated fatty acids, more preferably PUFAs chosen from the group consisting of eicosapentaenoic acid (EPA), docosahexaenoic acid (DHA), acid α-Linolenic acid (ALA) or combinations thereof.

PUFA's, in particular omega-3 PUFAs, have a specific capacity against triglyceride rich lipoproteins, remnant cholesterol and small dense LDL, whereas HMG CoA reductase inhibitors have no effect on remnant cholesterol, little efficacy towards triglyceride rich lipoproteins and CETP-inhibitors have no or little effect against triglyceride rich lipoprotein and remnant cholesterol. Hence, combining HMG CoA reductase inhibitors, CETP inhibitors and PUFAs in a pharmaceutical composition makes such a composition particularly suitable for the treatment of subjects suffering from or having an increased risk for cardiovascular diseases.

The PUFAs are preferably present in their free acid form, i.e. not in the form of ethyl esters in which the PUFA species are present in substantially esterified form. When the PUFAs are used in this form, the HMG CoA reductase inhibitors are better soluble in said PUFAs. In this regard reference is made to WO2013/169797, which document is herewith incorporated by reference.

The pharmaceutical composition according to the present invention comprises besides Compound A and the at least one HMG CoA reductase inhibitor also a pharmaceutically acceptable excipient, i.e. a pharmaceutically acceptable ingredient, which is commonly used in the pharmaceutical technology for preparing granulate, solid or liquid oral dosage formulations.

Examples of categories of excipients include, but are not limited to, binders, disintegrants, lubricants, glidants, fillers and diluents. One of ordinary skill in the art may select one or more of the aforementioned excipients with respect to the particular desired properties of the granulate and/or solid oral dosage form by routine experimentation and without any undue burden. The amount of each excipient used may vary within ranges conventional in the art. The following references which are all hereby incorporated by reference disclose techniques and excipients used to formulate oral dosage forms. See "The Handbook of Pharmaceutical Excipients", 4th edition, Rowe et al., Eds., American Pharmaceuticals Association (2003); and "Remington: The Science and Practice of Pharmacy", 20th edition, Gennaro, Ed., Lippincott Williams & Wilkins (2000).

A second aspect of the present relates to a therapeutic combination comprising
(a) a compound of the formula:

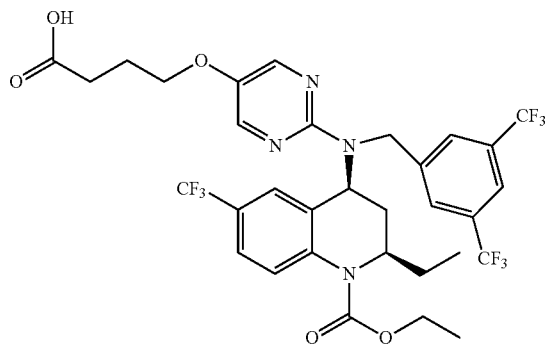 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

(hereinafter: Compound A) or a pharmaceutically acceptable salt thereof;
(b) at least one HMG CoA reductase inhibitor or a pharmaceutically acceptable salt thereof.

Preferably, the HMG CoA reductase inhibitor of said therapeutic combination is selected from the group consisting of atorvastatin, pravastatin, fluvastatin, simvastatin, lovastatin, rosuvastatin and pitavastatin.

More preferably, the HMG CoA reductase inhibitor is selected from the group consisting of atorvastatin calcium, pravastatin sodium, fluvastatin sodium, simvastatin, lovastatin and rosuvastatin calcium.

In a preferred embodiment the combination comprises about 1 to 25 mg of Compound A and about 1 to 80 mg of the HMG CoA reductase inhibitor. Alternatively, the pharmaceutical composition according to the present invention comprises 1 to 25 mg of Compound A and 1 to 50 mg, optionally 1 to 30 mg or 1 to 20 mg of the HMG CoA reductase inhibitor. In a further embodiment of the therapeutic combination according to the present invention the combination comprises 5 to 10 mg of Compound A and 1 to 20 mg of HMG CoA reductase inhibitor.

Due to the synergistic effect between Compound A and HMG CoA reductase inhibitors it is now also possible to lower the amount of HMG CoA reductase inhibitors used, thereby avoiding side effects commonly observed in these kinds of pharmaceutical compounds. In this regard it is also noted that such lower doses could also overcome intolerance to HMG CoA reductase inhibitors, which is also referred to as statin intolerance.

The therapeutic combination according to the present invention is preferably formulated as a fixed dose combination or a free dose combination, preferably a fixed dose combination.

In an alternative embodiment of the present invention the combination comprises a first unit dosage form comprising about 1 to 25 mg of Compound A or a pharmaceutically acceptable salt thereof and a second unit dosage form comprising about 1 to 80 mg of atorvastatin, pravastatin, fluvastatin, simvastatin, lovastatin, rosuvastatin, pitavastatin or a pharmaceutically acceptable salt thereof. The first and second unit dosage forms are in such a case preferably provided as a kit of parts. Preferably said combination comprises in such a case a package comprising said unit dosage forms.

The combination according the present invention may comprise polyunsaturated fatty acids (PUFAs), preferably omega-3 polyunsaturated fatty acids, more preferably PUFAs chosen from the group consisting of eicosapentaenoic acid (EPA), docosahexaenoic acid (DHA), acid α-Linolenic acid (ALA) or combinations thereof.

PUFA's, in particular omega-3 PUFAs, have a specific capacity against triglyceride rich lipoproteins, remnant cholesterol and small dense LDL, whereas HMG CoA reductase inhibitors have no effect on remnant cholesterol, little efficacy towards triglyceride rich lipoproteins and CETP-inhibitors have no or little effect against triglyceride rich lipoprotein and remnant cholesterol. Hence, combining HMG CoA reductase inhibitors, CETP inhibitors and PUFAs in a therapeutic combination makes such a combination particularly suitable for the treatment of subjects suffering from or having an increased risk for cardiovascular diseases.

The PUFAs are preferably present in their free acid form, i.e. not in the form of ethyl esters in which the PUFA species are present in substantially esterified form. When the PUFAs are used in this free acid form, the HMG CoA reductase inhibitors are better soluble in said PUFAs. In this regard reference is made to WO2013/169797, which document is herewith incorporated by reference.

A third aspect of the present invention relates to the use of the pharmaceutical composition or the therapeutic combination as described above in the treatment of subjects suffering from or having an increased risk for cardiovascular diseases.

The pharmaceutical composition or the therapeutic combination is preferably for use in the treatment of subjects suffering from or having an increased risk for hyperlipidemia or mixed dyslipidemia.

Preferably, a subject in need of the pharmaceutical composition or the therapeutic combination according to the present invention is administered by means of said composition or combination 1 to 25 mg per day of Compound A and 1 to 80 mg per day HMG CoA reductase inhibitor. Alternatively, a subject in need of said composition or combination is administered 1 to 25 mg of Compound A and 1 to 50 mg, optionally 1 to 30 mg or 1 to 20 mg of the HMG CoA reductase inhibitor. More preferably, the pharmaceutical composition or therapeutic combination is administered in such amounts that a subject in need thereof receives 1 to 25 mg per day of Compound A and 1 to 20 mg per day of the CoA reductase inhibitor.

In a further embodiment, the pharmaceutical composition or the therapeutic combination as described above are administered to subjects suffering from or having an increased risk for hyperlipidemia or mixed dyslipidemia in such amount that such a subject receives 1 to 25 mg per day of Compound A or a pharmaceutically acceptable salt thereof and 1 to 80 mg of atorvastatin, pravastatin, fluvastatin, simvastatin, lovastatin, rosuvastatin, pitavastatin or a pharmaceutically acceptable salt thereof.

The pharmaceutical composition or therapeutic combination according to the present invention is generally administered to subjects in need thereof for at least one week, preferably at least three weeks.

The present invention will be illustrated further by means of the following non-limiting example.

EXAMPLE

Double Blind Randomized Study of Subjects Receiving Compound A and Receiving Compound A in Combination with Statins In a double-blind, placebo controlled clinical study the effects of 12 weeks of administration of Compound A alone and in combination with statins in patients with mild dyslipidemia was examined.

Patients

This randomised, double-blind, placebo-controlled, parallel-group phase 2 trial was conducted in male and female patients (18-75 years) with fasting LDL-C levels >2·5 mmol/L and <4·5 mmol/L, HDL-C levels <1~8 mmol/L and >0·8 mmol/L and TG levels <4·5 mmol/L after run-in, or washout of existing therapies. Key exclusion criteria included patients with clinical manifestation of atherosclerotic vascular disease, type 1 diabetes, uncontrolled type 2 diabetes (haemoglobin A1c≥8%), uncontrolled hypertension, history of hyperaldosteronism, active muscle disease or persistent creatine kinase >3× the upper limit of normal (ULN), clinically significant renal or hepatic dysfunction, or evidence of any other clinically significant non-cardiac disease. Patients were recruited at 20 sites in the Netherlands and Denmark. The trial was approved by Independent Ethics Committees, and each patient provided written informed consent. The trial was conducted in accordance with the principles of the Declaration of Helsinki and Good Clinical Practice Guidelines and the protocol was registered on ClinicalTrials.gov (NCT01970215).

Trial Design

The trial consisted of a screening visit, followed by a run-in phase of 4 weeks (or 6 weeks for patients that required a washout of existing lipid-lowering therapy). After the run-in phase, patients were randomly assigned to receive one of the following nine treatments: 1 mg, 2.5 mg, 5 mg or 10 mg of Compound A or matching placebo; 10 mg of Compound A plus atorvastatin (20 mg), 10 mg of Compound A plus rosuvastatin (10 mg), atorvastatin (20 mg) or rosuvastatin (10 mg). All treatments were to be taken once daily with food for 12 weeks. During the double-blind treatment phase visits were conducted at baseline (Week 0) and at Weeks 4, 8 and 12. Follow-up visits were conducted 2 and 8 weeks after the end of treatment. Safety was assessed throughout the trial by monitoring adverse events and concomitant medication use, 12-lead electrocardiograms (ECGs), vital signs, laboratory safety assessments and physical examinations. Additional assessments included salivary cortisol, plasma aldosterone, high-sensitivity C-reactive protein (hsCRP) and endothelin 1.

Efficacy assessments included fasted lipid profiles including total cholesterol (TC), HDL-C, LDL-C, triglycerides, apolipoproteins AI, B and E (ApoAI, Apo B and ApoE), lipoprotein a (Lp[a]) and derived parameters. Exploratory endpoints included assessments of PCSK9, HDL-driven endothelial production of nitric oxide (NO), HDL particle numbers (using nuclear magnetic resonance [NMR] spectroscopy and ion mobility analysis), HDL particle subfractions (using 2D gel electrophoresis), CETP levels and activity, and insulin resistance (based on fasting plasma glucose and insulin levels using homeostasis model assessment insulin resistance [HOMA-IR] method). Blood samples were collected for pharmacokinetic analysis of Compound A.

Analytical Methods

Total cholesterol and triglycerides were measured by homogenous enzymatic assay using a Modular analyser (cholesterol oxidase peroxidase-peroxidase aminophenazone phenol [CHOP-PAP]) method and a glycerol phosphate oxidase [GPO-PAP] method, respectively. Apolipoproteins A1, A2, B and E were measured by immunoturbidimetry using reagents from Rolf Greiner Biochemica (Germany) and N apoprotein standard serum from Siemens (Germany). Lp(a) was measured by immunoturbidimetry using reagents and standards from Wako Chemicals (Germany). LDL particle size was determined by gradient gel electrophoresis. HDL fraction was separated by a combined ultracentrifugation-precipitation method ((β-quantification). HDL-2 and HDL-3 fractions were then separated by further ultracentrifugation. Total-cholesterol in HDL, HDL 2 and HLD-3 fractions, free cholesterol in HDL fraction, triglycerides in HDL fraction and phospholipids in plasma and HDL-fraction were measured using enzymatic methods and reagents from Diasys Diagnostics (Germany). The measurements were performed on an Olympus AU600 automatic analyzer and were calibrated using secondary standards from Roche Diagnostics (total-cholesterol, triglycerides) and Diasys Diagnostics (free cholesterol, phospholipids), respectively. Esterified cholesterol was calculated as the difference between total-cholesterol and free cholesterol.

Statistical Analysis

The co-primary efficacy endpoints were the percentage changes in both HDL-C and LDL-C levels at Week 12 compared to baseline. Secondary and exploratory efficacy endpoints included the percentage changes in other efficacy parameters at Week 12 compared to baseline. The primary and secondary efficacy analyses were performed using an analysis of covariance (ANCOVA) model with treatment and use of statin therapy at randomisation as factors and the baseline value for the respective efficacy variable as a covariate. Least-squares means, standard errors and 2-tailed 95% confidence intervals for each treatment group and for pairwise comparisons between Compound A doses and placebo, between Compound A plus atorvastatin and atorvastatin alone, and between Compound A plus rosuvastatin and rosuvastatin alone were provided. As there were two co-primary efficacy variables, a closed testing procedure was used in order to control the family-wise error. No interim analyses were planned or conducted.

The sample size of 37 completed patients per treatment group was intended to provide 88% power to detect a 22·5% (standard deviation [SD] 30%) increase in HDL-C compared with statin alone. This sample size with an assumed 10% (SD 15%) greater decrease in LDL-C for the investigational product compared with placebo was expected to provide a power of 80% for a successful study. All tests were 2-sided tests with a significance of 0·05. To allow for a 10-15% drop-out rate, 42 randomised patients per group were planned.

Results

The results of this clinical study are provided in table 1 and FIG. 1 below and reference is also made to Hovingh G.H, et al., Cholesterol ester transfer protein inhibition by TA-8995 in patients with mild dyslipidaemia (TULIP): a randomized, double-blind, placebo controlled phase 2 trial. *Lancet.* 2015., which article is herewith incorporated by reference.

From this table it is apparent that Compound A already at a relatively low dose significantly increases HDL-C concentration, decreases LDL-C concentrations and Lp(a) concentrations. It is further clear from these results that the administration of both Compound A and atorvastatin or rosuvastatin results in a synergistic effect with respect to the lowering of LDL-C concentrations. Furthermore, the combination of Compound A with a statin also showed a markedly increase of HDL-C and a remarkable decrease of Lp(a). Hence, the administration of Compound A in combination with a statin appears to be very beneficial for patients suffering from cardiovascular diseases, in particular dyslipidemia.

TABLE 1 results of the clinical study

|  | Placebo | 1 mg of Compound A | 2.5 mg of Compound A | 5 mg of Compound A | 10 mg of Compound A |
|---|---|---|---|---|---|
| n | 40 | 39 | 41 | 40 | 40 |
| HDL-C | 1.80 | 76.04 | 122.28 | 160.90 | 180.64 |
| LDL-C | 0.18 | −27.05 | −34.38 | −47.49 | −47.26 |
| Lp(a) | −5.06 | −28.81 | −26.69 | −37.33 | −34.86 |

|  | Atorvastatin | Atorvastatin + 10 mg of Compound A | Rosuvastatin | Rosuvastatin + 10 mg of Compound A | Total |
|---|---|---|---|---|---|
| n | 40 | 40 | 41 | 41 | 362 |
| HDL-C | 1.27 | 154.19 | 6.16 | 159.86 |  |
| LDL-C | −46.73 | −69.56 | −47.36 | −65.58 |  |
| Lp(a) | −4.46 | −25.29 | −7.79 | −24.16 |  |

It has further been found that Compound A alone and in combination with statins, such as rosuvastatin, enhanced the ability of serum to promote cholesterol efflux. The ability of serum to promote cholesterol efflux was increased by 16.9% (p<0.0001) in patients given 1 mg of Compound A, whereas treatment with the 10 mg dose of Compound A resulted in a 36.7% increase in serum-mediated cholesterol efflux (p<0.0001; FIG. 1).

In this Figure baseline and week 12 data for serum-driven cholesterol efflux is shown. Bars are means and error bars are standard deviations. The baseline data only includes patients who had both baseline and week 12 data. The changes from baseline for all active treatments showed significant differences from placebo at week 12.

Chemical Name and Formula of a Compound A

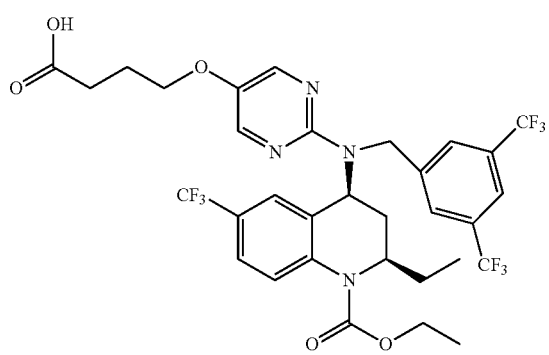 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

{4-[(2-{[3,5-bis(trifluoromethyl)benzyl][(2R,4S)-1-(ethoxycarbonyl)-2-ethyl-6-(trifluoromethyl)-1,2,3,4-tetra-hydroquinolin-4-yl]amino}pyrimidin-5-yl)oxy]butanoic acid}

The invention claimed is:

1. A pharmaceutical composition comprising:
   (a) a compound of the formula:

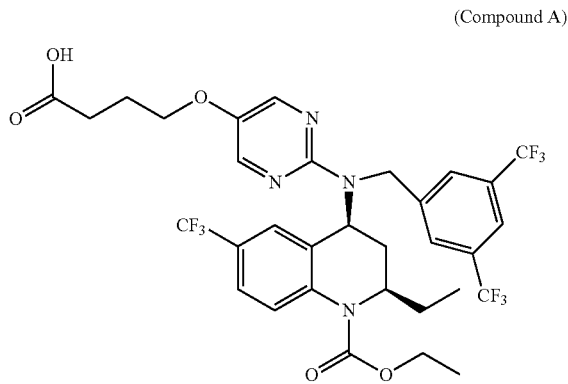 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

(Compound A)

or a pharmaceutically acceptable salt thereof;
   (b) at least one HMG CoA reductase inhibitor or a pharmaceutically acceptable salt thereof; and
   (c) one or more pharmaceutically acceptable excipients;
   wherein the composition comprises 1 mg to 25 mg of Compound A or a pharmaceutically acceptable salt thereof and 1 mg to 80 mg of the HMG CoA reductase inhibitor or a pharmaceutically acceptable salt thereof wherein the composition is formulated as an oral fixed dose combination for a once a day administration.

2. The pharmaceutical composition according to claim 1, wherein the HMG CoA reductase inhibitor is selected from the group consisting of atorvastatin, pravastatin, fluvastatin, simvastatin, lovastatin, rosuvastatin and pitavastatin.

3. The pharmaceutical composition according to claim 1, wherein the HMG CoA reductase inhibitor is selected from the group consisting of atorvastatin calcium, pravastatin sodium, fluvastatin sodium, simvastatin, lovastatin and rosuvastatin calcium.

4. The pharmaceutical composition according to claim 1, wherein the oral fixed dose combination is a solid dosage form.

5. The pharmaceutical composition according to claim wherein the composition is an oral fixed dose combination comprising 1 mg, 2.5 mg, 5 mg or 10 mg of Compound A and 10 mg to 20 mg of atorvastatin or rosuvastatin.

6. The pharmaceutical composition according to claim 1, wherein the composition comprises polyunsaturated fatty acids.

7. The pharmaceutical composition according to claim 6, wherein the polyunsaturated fatty acids are present in their free acid form.

8. The pharmaceutical composition according to claim 6, wherein the polyunsaturated fatty acids is omega-3 polyunsaturated fatty acids.

9. The pharmaceutical composition according to claim 8, wherein the omega-3 polyunsaturated fatty acids are selected from the group consisting of eicosapentaenoic acid (EPA), docosahexaenoic acid (DHA), α-Linolenic acid (ALA) or combinations thereof.

10. A method of treating a subject suffering from or having an increased risk for cardiovascular diseases comprising administering to said subject in need thereof a pharmaceutically effective amount of said pharmaceutical composition according to claim 1.

11. The method of claim 10, wherein said subject is suffering from or having an increased risk for hyperlipidemia or mixed dyslipidemia.

12. The method of claim 10, wherein said pharmaceutically effective amount of said pharmaceutical composition is 1 mg, 2.5 mg, 5 mg or 10 mg per day of Compound A and 10 mg to 20 mg per day of HMG CoA reductase inhibitor.

13. The method of claim 12, wherein the HMG CoA reductase inhibitor is selected from the group consisting of atorvastatin, pravastatin, fluvastatin, simvastatin, lovastatin, rosuvastatin and pitavastatin.

14. The method of claim 11, wherein said pharmaceutically effective amount of said pharmaceutical composition is al mg, 2.5 mg, 5 mg or 10 mg per day of Compound A, or a pharmaceutically acceptable salt thereof, and 10 mg to 20 mg per day of atorvastatin or rosuvastatin, or a pharmaceutically acceptable salt thereof.

15. The method of claim 11, comprising administering to said subject in need thereof a pharmaceutically effective amount of said pharmaceutical composition for at least one week, or at least three weeks.

* * * * *